United States Patent [19]

Nowak

[11] Patent Number: 5,827,522
[45] Date of Patent: Oct. 27, 1998

[54] MICROEMULSION AND METHOD

[75] Inventor: Milton Nowak, South Orange, N.J.

[73] Assignee: Troy Corporation, Florham Park, N.J.

[21] Appl. No.: 741,038

[22] Filed: Oct. 30, 1996

[51] Int. Cl.$^6$ .............................. A01N 25/00; A61K 9/107
[52] U.S. Cl. .......................... 424/405; 424/400; 514/937
[58] Field of Search .................................... 424/400, 405; 514/937, 938, 390, 521

[56] References Cited

U.S. PATENT DOCUMENTS

| | | | |
|---|---|---|---|
| 4,567,161 | 1/1986 | Posanski et al. | 514/23 |
| 4,904,695 | 2/1990 | Bell | 514/521 |
| 4,954,338 | 9/1990 | Mattox | 424/78 |
| 4,973,352 | 11/1990 | Heinrich et al. | 71/91 |
| 5,013,748 | 5/1991 | Radtke et al. | 514/383 |
| 5,037,653 | 8/1991 | Dawson | 424/405 |
| 5,156,666 | 10/1992 | Narayanan et al. | 71/79 |
| 5,242,907 | 9/1993 | Dawson | 514/65 |
| 5,407,920 | 4/1995 | Dawson | 514/65 |
| 5,428,050 | 6/1995 | Merianos | 514/390 |
| 5,597,840 | 1/1997 | Moore | 514/365 |
| 5,612,047 | 3/1997 | Duffey et al. | |

FOREIGN PATENT DOCUMENTS

| | | |
|---|---|---|
| 0 427 582 | 5/1991 | European Pat. Off. . |
| 0 472 973 A1 | 3/1992 | European Pat. Off. . |
| 0 648 414 A2 | 4/1995 | European Pat. Off. . |
| 5039202 | 2/1980 | Japan . |
| 59-026906 | 2/1984 | Japan . |
| 60-175914 | 9/1985 | Japan . |
| 646 306 | 10/1980 | Switzerland . |
| WO 88/07326 | 10/1988 | WIPO . |
| WO 90/03111 | 4/1990 | WIPO . |
| WO 90/03112 | 4/1990 | WIPO . |
| WO 93/14630 | 8/1993 | WIPO . |
| WO 95/15081 | 6/1995 | WIPO . |

OTHER PUBLICATIONS

Skelton et al., "Formulation of Pesticide Microemulsions," Astm. Spec. Tech. Bull., Pestic. Formulations Appl. Syst., vol. 8, No. 980, 36–45, 1989.
International Search Report mailed Feb. 6, 1998.
Yu et al., "Fully Water–Dilutable Microemulsions", *CA Selects: Antibacterial Agents* 14:6 (1995) Abstract 122:308763q.
Cremophor El Technical Leaflet.

*Primary Examiner*—Michael P. Woodward
*Assistant Examiner*—Brenda G. Brumback
*Attorney, Agent, or Firm*—Banner & Witcoff, Ltd.

[57] ABSTRACT

A water miscible composition consisting essentially of a solvating surfactant selected from the group consisting of an alkoxylated castor oil, an alkoxylated hydrogenated castor oil and an alkoxylated rosin, and a biocidal biologically active material dissolved in said solvating surfactant useful to prepare aqueous microemulsions, micellar solutions or molecular solutions of said biocidal biologically active material upon mixing with water.

16 Claims, No Drawings

MICROEMULSION AND METHOD

BACKGROUND OF THE INVENTION

1. Field of the Invention

This invention broadly relates to the preparation of microemulsions of biologically active, and often labile, materials. In a preferred aspect, this invention relates to the preparation of biocidal concentrates which can be used to prepare aqueous microemulsions of fungicides useful in the protection of wood surfaces or for incorporation into metal working fluids, and to prepare aqueous microemulsions for use as insecticides, herbicides, slimicides, or algaecides.

2. Description of Related Art

Microemulsions are dispersions of one liquid phase in a second immiscible phase. They can be water continuous (o/w) or oil continuous (w/o) where "oil" denotes an organic liquid (or liquids) of low water solubility. A unique property of microemulsions is that the interfacial tension between the two phases is very low. In the prior art, obtaining this low interfacial tension was thought to require very specific combinations of "oil" (water immiscible organic liquid) and surfactants and water. The particle size of the dispersed phase of a microemulsion is extremely small, usually less that 1000–2000 Å. Since this size is small in relation to the wave length of visible light, microemulsions appear opalescent or more usually optically clear. Microemulsions typically are stable against phase separation for long time periods, e.g. often times for periods measured in years. In contrast, normal macroemulsions, where a milky appearance results from emulsion particles being in the 1–20 $\mu$ range, phase separation typically occurs within hours to weeks after the emulsion is prepared.

As described in the prior art, optimum solubilization of an oil to give an o/w microemulsion occurs within a narrow composition range of oil, surfactant, cosurfactant and water. Some investigators have stressed the essential role played by a co-surfactant in the formation of a microemulsion. *J Am. Chem. Soc.*, (1991), 113: 9621–9624.

A typical example is given in *Microemulsion Theory and Practice*, Ed. L. M. Prince, Academic Press (1977) describing the system p-xylene, sodium lauryl sulfate, pentanol and water. In fact, the prior art indicates that the use of several surfactants is usually required to produce a microemulsion. When one of the surfactants is soluble in the water phase and the other is soluble in the organic phase, each one has only a marginal effect on the other, and their combined effect may be large enough to reduce the interfacial tension to near zero at finite concentrations. Thus, although microemulsions are obtainable with certain surfactant combinations and within finite concentration ranges of these surfactant combinations, at present, formulating such microemulsions is essentially still an art. When the composition is outside the microemulsion range, as defined by a phase diagram, multiphase regions exist. The consequence is that dilution of a microemulsion composition with water often leads to formation of a macroemulsion or multiphase, unstable systems. In a practical sense it is desirable to define a microemulsion composition that will remain clear and not phase separate when further diluted with water.

An oil in water micellar solution can result when a small amount of "oil" is added to an aqueous solution of a surfactant and water. If the amount of surfactant is great in relation to the "oil" (say>5:1), the oil can migrate to the interior of a surfactant micelle without greatly disturbing it. Such solubilizing of the oil in a surfactant micelle can result in a clear micellar solution and the solution will very often retain clarity when further diluted in water. Because of the large excess of surfactant in such micellar solutions, the proportions of the various constituents in such compositions are not as critical as with microemulsions. Even so, a microemulsion represents a much more efficient way of solubilizing an oil.

European Patent Application 0648414 describes the preparation of a microemulsion concentrate containing a nonpolar water immiscible solvent, at least one ethoxylated surfactant and at least one sulfated anionic cosurfactant. The concentrate is fully water dilutable to form a microemulsion.

U.S. Pat. No. 5,242,907 involves the use of a formulation of microemulsions comprising an oil, a surfactant, and a co-surfactant. This patent deals primarily with forming a microemulsion of cypermethrin, a pyrethoid-type material.

U.S. Pat. No. 5,444,078 describes mixtures of active ingredients that are substantially insoluble in water combined with a water immiscible solvent for the active ingredients, and a surfactant-cosurfactant system composed of sulfonated ionic surfactants and ethoxylated alcohols.

WO 93/14630 describes the treatment of timber with microemulsions containing pesticides such as pyrethroids, or fungicides such as iodopropargyl butyl carbonate (IPBC) and/or propiconazole. The formulations include an oil, together with a surfactant, a co-surfactant and sodium hydroxide and calcium chloride.

U.S. Pat. No. 5,013,748 is concerned with the preparation of liquid organic concentrates, and emulsions and microemulsions made therefrom, produced using as the active biocidal ingredients a very specific set of triazol fungicides and quaternary ammonium fungicides, and at least one benzimidazole fungicide mixed with one or more isothiazolones, together with a liquid carrying agent composed of an alkanol of up to six carbon atoms and a saturated monocarboxylic acid containing from one to six carbon atoms.

U.S. Pat. No. 4,973,352 claims the preparation of microemulsions of herbicides such as phenoxyphenoxycarboxylic acid ester combined with a salt of bentazone (3-isopropyl-1H-benzo-2,1,3-thiadiazin-y-one 2,2-dioxide) using at least one emulsifier and one or more organic solvents. The examples cited contain, in every case, at least two emulsifiers.

U.S. Pat. No. 4,954,338 describes microemulsions of isothiazolones prepared with the use of an anionic surfactant together with a non-ionic co-surfactant and a polyoxyethylene-polyoxypropylene block copolymer.

U.S. Pat. No. 4,904,695 relates to the preparation of microemulsions of insecticides in formulations containing a surfactant blend, a thickening agent, an anti-freeze and a defoamer.

WO 90/03111 is directed to the use of siloxane based surfactants for the preparation of microemulsions of pyrethroids. It requires the use of water, oil, a surfactant and a co-surfactant.

WO 90/03112 describes a method of protecting crops by treating them with a microemulsion prepared from a pyrethroid pesticide, an oil, a surfactant and a co-surfactant.

U.S. Pat. No. 5,037,653 (WO 88/07326) describes the preparation of ready-to-use microemulsions consisting of a pesticide, water, an anionic cosurfactant, a non-ionic surfactant and oil. It does not describe preparation of base solutions e.g., a concentrate, which can be diluted with water or added to water to form a microemulsion.

U.S. Pat. No. 4,567,161 is directed to the preparation of microemulsions of herbicides, fungicides, etc., through the use of a combination of phospholipids and a co-surfactant consisting of an ethoxylated glycerin ester.

It will be realized that there is a plethora of prior art for the preparation of microemulsions. In the main, however, the prior art teaches that an oil or water-immiscible solvent, a surfactant, usually a non-ionic surfactant, and a co-surfactant (usually an anionic surfactant) are required.

The amount of surfactant required, as indicated in these prior art formulations, generally varies from about 10 times the weight of the labile ingredient, e.g., a pesticide, up to about 200 times its weight. In certain prior art disclosures, the stability of the microemulsion is not considered or reported. In most of the prior art disclosures, the preparation of the microemulsion is carried out by separately adding each ingredient to the full complement of water, a procedure that often is not practical for industrial or agricultural applications.

BRIEF DESCRIPTION OF THE INVENTION

The present invention involves the use of a single surfactant which simultaneously acts as a solvent for the biologically active, and generally labile biocidal compound, such as a fungicide (iodopropargyl butyl carbamate (IPBC) for example), and which by itself yields a stable microemulsion, a micellar solution or a molecular solution on mixing with water. Such materials are referred to herein as "solvating surfactants." No co-surfactants are needed, and preferably no co-surfactants are employed to produce a stable, water miscible composition. Use of an additional water immiscible solvent, an oil, a non-polar solvent, etc., is also unnecessary, though such a constituent may be advantageous in some circumstances as hereinafter described.

Consequently, the present invention is directed, in a first aspect, to a water miscible composition or concentrate consisting essentially of a solvating surfactant selected from the group consisting of an alkoxylated castor oil, an alkoxylated hydrogenated castor oil and an alkoxylated rosin, and having a biologically active, biocidal material dissolved in said solvating surfactant. The present invention also is directed to a microemulsion, a micellar solution or a molecular solution of the biologically active biocidal material prepared simply by adding water to the above-described concentrate composition and mixing.

The class of solvating surfactants employed in the present invention, i.e., alkoxylated, e.g., ethoxylated castor oils, alkoxylated, e.g., ethoxylated hydrogenated castor oil and alkoxylated, e.g., ethoxylated rosin, are good solvents for a variety of generally labile biocidally active compounds including IPBC; benzisothiazolones; propaconazole; propiconazole (CAS-60207-90-1); permethryn (CAS-52645-53-1), [(3-(2,2-dichloroethenyl)-2,2-dimethylcyclopropane carboxylic acid (3-phenoxyphenyl)-methyl ester)]; deltamethrin (CAS-52918-63-5) [(3-(2,2-dibromoethenyl)-2,2-dimethyl-cyclopropane carboxylic acid cyano (3-phenoxyphenyl) methyl ester]; cypermethrin (CAS-52315-07-8) [(3-(2,2-dichloroethenyl)-2,2-dimethylcyclopropane carboxylic acid cyano (3-phenoxyphenyl) methyl ester)]; chlorpyriphos (CAS-2921-88-2) [(Allethrin)(0,0-diethyl O-(3,5,6Trichloro-2-pyridinyl) phosphorothiate)]; tebuconazole (CAS-107534-96-3); 8-hydroxyquinoline (CAS-148-24-3); 2-(hydroxymethylamino) ethanol (CAS-65184-12-5); iodopropynyl cyclohexyl carbamate; Irgarol (n-cyclopropynyl-$N^1$-(1,1-dimethylethyl)-6-(methylthio)-1,3,5-triazine-2,4-diamine); 2,4-dichloro phenoxyacetic acid, butyl ester; 2,4,5-trichlorophenoxy acetic acid, ethyl ester; 2,4 dichlorbutyric acid, ethyl ester; Chlordane; piperonyl butoxide; bromoxynil (3,5-dibromo-4-hydroxy benzonitrile ester of n-octanoic acid); Thanite®: isobornylthiocyanoacetate; iodo propargyl succinate; terbutryn (CAS-886-50-0)[(2-tert-butylamino-4-ethylamino-6-methylthio-1,3,5 -triazine)]; 5-chloro-2-methyl-4-isothiazolin-3-one, 2-methyl-4-isothiazolin-3-one; 1,4-dichloro-2,5 -dimethoxy benzene (Chloroneb); orthophenylphenol; azaconazole; cyperconazole; Amical (diiodomethyl-p-tolyl sulfone); IF-1000 (iodopropynyl phenylether); Cyfluthrin (CAS-68359-37-5); beta cyfluthrin (CFAS68359-37 -5); lambda-cyhalothrin (CAS-91465-08-6); cyhexatin (CAS-13121-70-5); cyphenothrin (CAS-39515-40-7); endosulfan (CAS-115-29-7); (1,4,5,6,7,7-hexachloro 8,9,10-trinorborn-5 -en-2,3-ylene bismethylene) sulfide (IUPAC); fenitrothion (CAS-122-14-5); and many other bactericides, fungicides, herbicides, algacides, acaricides, and the like, or combinations of two or more of these materials.

In its broadest aspect, the present invention is directed to preparing a microemulsion of any biocidal material that is water insoluble, but which can be dissolved in the solvating surfactant of the present invention.

To prepare the concentrate composition of the invention, the biocidal biologically active material, such as a pesticide, is dissolved in the solvating surfactant, such as an ethoxylated castor oil, at room temperature or at a slightly elevated temperature such as in the range of 50°–75° C. Solutions of the biocidal material in the solvating surfactant containing up to about 25% by weight of the biocidally active material may be prepared, depending upon the individual material. Combinations of two or more of the biocidal biologically active materials also may be dissolved in the aforementioned solvating surfactants to form a concentrate solution which yields a microemulsion, a micellar solution or a molecular solution when mixed with water. The aqueous compositions formed from mixing the concentrate with water are clear solutions that remain stable for periods up to two months or more. Microemulsions of this invention are generally stable indefinitely. In an alternate embodiment, an oil or an organic solvent also may be included in the concentrate composition to reduce its viscosity at high solute concentrations.

DETAILED DESCRIPTION OF THE INVENTION

Castor oil is a pale yellow to colorless, transparent viscous liquid obtained by cold-pressing the seeds of the castor bean, *Ricinus communis*. By far, the chief component of the fixed oil is the triglyceride (ester) of ricinoleic acid, with minor amounts of oleic, linoleic, palmitic and stearic acid glycidal esters. Ricinoleic acid is a $C_{18}$, unsaturated (hydroxy) fatty acid. Hydrogenation of castor oil produces a hard, white wax having a molecular weight of about 932 and a melting point of 86°–88° C. Rosin is mainly composed of resin acids of the abietic and pimaric types.

Alkoxylated castor oil, alkoxylated hydrogenated castor oil and alkoxylated rosin are prepared by reacting the oil with an alkylene oxide under conditions well known to those skilled in the art. The ethylene oxide adducts of castor oil, hydrogenated castor oil and rosin are widely available commercially. In particular, ethoxylated castor oil is available from Chemiax Inc. as Chemax CO-30, CO40, and CO-80; from Witco Corp. as DeSonic 30C and 40C from Rhone-Poulenc as Alkamuls CO-40; from Henkel Inc. as Trylons and from Cas Chem., Inc. and BASF.

In the context of the present invention the "biocidal biologically active material" is any compound having microbiocidal activity, e.g., fungicidal, bactericidal and the like activity, herbicidal activity, e.g., algaecidal and the like activity, pesticidal activity, e.g., acaricidal, insecticidal, miticidal, and the like activity, or plant growth regulating activity. Generally, the solubility of the active material in water is less than 10,000 ppm and more often is less than 1000 ppm at room temperature. The biocidally active material also is soluble in the solvating surfactant in an amount of at least about 10 weight percent, and preferably at least about 15 weight percent. It is unlikely that the concentration of the biocidally active material in the solvating surfactant will exceed 40%. The actual limit on the concentration of the biocidally active material in the solvating surfactant is determined by its solubility in the surfactant and the optional use of a co-solvent. More usually, the concentrate composition will contain from about 5 to 25 weight percent of the biocidal active material.

Suitable candidates for the active material are IPBC; benzisothiazolones; propaconazole; propiconazole (CAS-60207-90-1); permethryn (CAS-52645-53 -1), [(3-(2,2 -dichloroethenyl)-2,2-dimethylcyclopropane carboxylic acid (3-phenoxyphenyl)-methyl ester)]; deltamethrin (CAS-52918-63-5) [(3-(2,2-dibromoethenyl)-2,2-dimethyl-cyclopropane carboxylic acid cyano (3-phenoxyphenyl) methyl ester]; cypermethrin (CAS-52315-07-8) [(3-(2,2-dichloroethenyl)-2,2-dimethylcyclopropane carboxylic acid cyano (3-phenoxyphenyl) methyl ester)]; chlorpyriphos (CAS-2921-88-2) [(Allethrin)(0,0-diethyl O-(3,5,6-Trichloro-2-pyridinyl) phosphorothiate)]; tebuconazole (CAS107534-96-3); 8-hydroxyquinoline (CAS-148-24-3); 2-(hydroxymethylamino) ethanol (CAS-65184-12-5); iodopropynyl cyclohexyl carbamate; Irgarol (n-cyclopropynyl-$N^1$-(1,1-dimethylethyl)-6 -(methylthio)-1, 3,5-triazine-2,4-diamine); 2,4-dichloro phenoxyacetic acid, butyl ester; 2,4,5-trichlorophenoxy acetic acid, ethyl ester; 2,4 dichlorbutyric acid, ethyl ester; Chlordane; piperonyl butoxide; bromoxynil (3,5-dibromo-4-hydroxy benzonitrile ester of n-octanoic acid); Thanite®: isobornylthiocyanoacetate; iodo propargyl succinate; terbutryn (CAS-886-50-0)[(2-tert-butylamino-4 -ethylamino-6-methylthio-1,3,5-triazine)]; 5-chloro-2-methyl-4-isothiazolin-3-one, 2-methyl-4-isothiazolin-3-one; 1,4-dichloro-2,5-dimethoxy benzene (Chloroneb); orthophenylphenol; ~(RS) -3-allyl-2 -methyl-4 okocyclopent-2-enyl (IRS) Cu; trans chrysan the math (IUPAC); azaconazole; cyperconazole; Amical (diiodomethyl-p-tolyl sulfone); IF-1000 (iodopropynyl phenylether); Cyfluthrin (CAS-68359-37-5); beta cyfluthrin (CFAS-68359-37-5); lambda-cyhalothrin (CAS-91465-08-6); cyhexatin (CAS-13121-70-5); cyphenothrin (CAS-39515-40-7); endosulfan (CAS-115-29-7); (1,4,5,6,7,7-hexachloro 8,9,10-trinorborn-5-en-2,3-ylene bismethylene) sulfide (IUPAC); fenitrothion (CAS-122-14-5).

Other materials which function as binders, film formers, or catalysts such as cobalt octoate 12% (cobalt salt of 2-ethylhexanoic acid diluted to 12% cobalt metal in mineral spirits.), alkyd resins (60% solution in mineral spirits) and urea-formaldehyde resins (CAS-28931-47-7) may be incorporated in the emulsion base either individually of in combination with one or more biologically active materials.

As illustrated in the examples which follow, the concentrate compositions of the present invention are improved by including an additional co-solvent oil such as castor oil, linseed oil olive oil, and the like or other solvents such as toluene, xylene, super high flash naphtha and ethyl benzene. In particular, by adding castor oil to a composition of an ethoxylated castor oil and IPBC the stability of any microemulsion, micellar solution or molecular solution made using the concentrate is enhanced. Without the added castor oil, a higher ratio of alkoxylated castor oil solvating surfactant to active biocide is required to yield a stable concentrate composition that can be mixed with water to provide a suitable microemulsion, micellar solution or molecular solution. With the added castor oil, the concentrate composition can contain a higher content of the biocidal material. Sources of castor oil based surfactants include: Cremophor El and Cremophor RH 410 (BASF); Trylon 5909 (Henkel); and Surfactol 365. Surfactant AR-150 (Hercules, Inc.) can be used as an ethoxylated resin surfactant.

The concentrate composition generally will be mixed with water in an amount of from 1:1 parts by weight water to parts by weight concentrate up to about 1000:1 water to concentrate, and more usually in the range of from 10:1 to 100:1. Consequently, the concentration of biocidal material in the aqueous composition will generally fall between about 0.01 to 10 percent by weight and more usually 0.1 to 1 weight percent.

The water miscible biocidal concentrate compositions of the present invention have potential application in a variety of circumstances including, but not limited to disinfectants, sanitizers, cleaners, deodorizers, liquid and powder soaps, skin removers, oil and grease removers, food processing chemicals, wood preservation, polymer latices, paint lazures, stains, mildewcides, hospital and medical antiseptics, medical devices, metal working fluids, cooling water, air washers, petroleum protection, paper treatment, pulp and paper slurries, paper mill slimicides, petroleum products, adhesives, textiles, pigment slurries, latexes, leather and hide treatment, petroleum fuel, jet fuel, laundry sanitizers, agricultural formulations, inks, mining, non-woven fabrics, petroleum storage, rubber, sugar processing, tobacco, swimming pools, photographic rinses, cosmetics, toiletries, pharmaceuticals, chemical toiletries, household laundry products, diesel fuel additives, waxes and polishes, oil field applications, and many other applications where water and organic materials come in contact under conditions which allow the growth of undesired microorganisms.

The following examples are presented to illustrate and explain the invention. Unless otherwise indicated, all references to parts and percentages are based on weight.

EXAMPLE 1

An ethoxylated castor oil (90 g.) (CAS No. 61791-12-6) (an ethoxylated castor oil containing 40 moles of ethylene oxide) is warmed to 30° C. while agitating. Iodopropargyl butyl carbamate (IPBC) (10 g) (CAS No. 55406-53-6), a well-known fungicide, is added with agitation. The mixture is stirred until the IPBC is completely dissolved. The solution then is allowed to cool gradually to room temperature. The product is a clear pale amber viscous solution containing 10% by weight of IPBC. The solution (1.25 g) is dissolved in tap water (24 g.) to yield a clear microemulsion containing 0.5% IPBC.

EXAMPLE 2

Ethoxylated castor oil (80 g) (containing 40 mols of ethylene oxide) is mixed with 2-(hydroxymethylamino) ethanol, 12 g (CAS No. 65184-12-5) a liquid bactericide (sold under trade name Troysan 174). After a homogeneous solution is formed, IPBC (12 g) is added and the mixture is stirred until the IPBC is completely dissolved. This composition (1.0 g) was added with agitation to tap water (22.5 g) to yield a clear microemulsion containing 0.5% IPBC and 0.5% 2 -(hydroxymethylamino) ethanol.

EXAMPLE 3

1,2-benzisothiazolin-3-one (10 g.) was added to an ethoxylated castor oil (90 g.) (40 mols of ethylene oxide) and the mixture was warmed to 35° C. and stirred until a clear solution was obtained. The product was a clear, light amber solution containing 10% of the preservative, 1-2-benzisothiazolin-3-one.

This product (1.25 g.) was added to tap water (24 g.) while stirring to yield a clear microemulsion containing 0.5% 1,2-benzisothiazolin-3-one.

EXAMPLE 4

Permethrin (5 g.) was dissolved in an ethoxylated castor oil (90 g.) (40 mols of ethylene oxide) to form a clear, slightly viscous liquid.

This solution (1.25 g.) then was added to tap water (24 g.) to form a 0.25% active microemulsion.

EXAMPLE 5

IPBC (6.6 g.) and terbutryn (3.4 g.) were added to an ethoxylated (40 mols) castor oil (90 g.). The mixture was warmed to 30° C. and stirred until solution was complete. The product was a light, amber solution. This solution (1.25 g.) was added to tap water (24 g.) to form a microemulsion containing 0.165% terbutryn and 0.34% of IPBC.

EXAMPLE 6

Iodopropargyl butyl carbamate (IPBC) (10 g.) was dissolved in an ethoxylated hydrogenated castor oil (90 g.) by warming to 50° C. On cooling, the product changed to a pasty white solid containing 10% of IPBC.

The pasty solid was added to water (23.75 g.) with agitation to produce a clear solution containing 0.5% of IPBC.

EXAMPLE 7

IPBC (11 g.) was dissolved in an ethoxylated rosin (CAS No. 8050-33-7) (89 g.) by warming the mixture at 45° C. An amber colored solution containing 11% IPBC was obtained.

This product (1.1 g.) was dissolved in water (23.9 g.) to yield a clear, very pale amber solution containing 0.5% IPBC.

EXAMPLE 8

IPBC, 15 g is dissolved in 55 g of Cremophor EL and 30 g of Castor Oil. (Cremophor E1 is an ethoxylated castor oil containing 35 moles ethylene oxide to one mole castor oil) the concentrated product is a pale amber liquid containing 15% IPBC.

The concentrated product (3.3 g) is added to 96.7 g of water and stirred to yield a clear aqueous solution containing 0.5% IPBC. There has been no sign of precipitation nor turbidity after one month's storage.

EXAMPLE 9

IPBC (10 g.) was dissolved by agitation at room temperature in an ethoxylated castor oil (80 g.). To this solution was added an alkyd resin solution (10 g.) having 60% solids dissolved in a super high flash naphtha. The product is a clear very pale amber solution.

This product (1.25 g.) was added to water (23.75 g.) to yield a clear solution containing 0.5% IPBC, and has remained stable for more than two months.

Another portion of this product, (0.62 g.) was further added to water (24.4 g.) to yield a clear solution containing 0.25% IPBC, and has also remained stable for more than two months.

EXAMPLE 10

10 g of Castor Oil, 7.0 g, IPBC, and 3 g Propiconazole were added to 90 g of an ethoxylated (40 mols) Castor Oil (Surfactol 365, a product of Cas Chem., Inc., CAS No. 61791-12-6).

The mixture was warmed to 30° C. and stirred until a clear solution was obtained. The concentrate product, a clear pale amber solution, contained 3% of Propiconazole and 7% IPBC.

0.62 g of this solution was added to 24.4 g of tap water. The mixture was stirred until a perfectly clear microemulsion was obtained containing a total of 0.25% active ingredients—(30% Propiconazole, 70% IPBC).

EXAMPLE 11

3.3 g Irgarol, 6.7 g IPBC and 30 g, Castor oil were mixed with 60 g ethoxylated (40 mols) Castor oil. The mixture was heated to 30° C. and stirred until a clear solution was obtained.

1.25 g of the concentrated product, a clear pale amber liquid, was mixed with 23.75 g tap water. A clear water-like microemulsion was obtained containing 0.5% active ingredients. This microemulsion was stored at room temperature and has remained clear for 2 weeks.

EXAMPLE 12

2 g of IPBC was dissolved in 7 g Cremophore RH-40 (Ethoxylated Hydrogenated Castor oil containing 40 moles Ethylene Oxide) by warming to 45° C. When solution was complete, 1 g of Castor oil was added. The product is a clear pasty liquid containing 20% IPBC.

1.25 g of this product was added to 98.75 g water with rapid agitation to yield a clear solution containing 0.25% IPBC. This solution has remained clear for one month.

EXAMPLE 13

IPBC, 10 g was dissolved in a solution consisting of Super High Flash Naphtha, 5 g, and Trylon 5909 (Product of Henkel Corp.) (CAS#61791-12-6), 85 g. by agitation at room temperature. The concentrate product, a very pale amber liquid, contains 10% IPBC.

5 g of this product was added, with agitation, to 95 g water to yield a clear microemulsion.

EXAMPLE 14

Terbutryn (3 g.) (2-(tert-butylamino) -4-(ethylamino)-6-(methylthio)-S-triazine) (CAS No. 886-50-0) was dissolved in an ethoxylated castor oil (80 g.) by warming and agitating the mixture at 30° C. There was then added castor oil (10 g.) and IPBC (7 g.). The mixture was agitated until solution was complete. The product, a clear liquid, contained 7% IPBC and 3% terbutryn.

This clear liquid product (1.25 g.) was mixed with water (23.75 g.) to yield a clear solution containing 0.15% terbutryn and 0.35% IPBC. The solution has remained stable for more than two months.

EXAMPLE 15

IPBC 15 g, was dissolved in a solution consisting of toluene, 7 g, and Surfactol 365, 78 g, by agitating at 35° C. A clear very pale amber solution containing 15 % IPBC was obtained.

33 g of this solution was placed in a 200 ml beaker and agitated while 67 g of water was added. At first the solution increased in viscosity, but quickly formed a clear microemulsion containing 5.0% IPBC.

EXAMPLE 16

7 g IPBC and 3 g of 8-Hydroxyquinoline are added to 90 g Surfactol 365 and the mixture stirred while warming to 50° C. A clear light amber solution was obtained containing 7% IPBC and 3% 8-Hydroxyquinoline.

3 g of this solution was added to 97 g water while stirring. A clear microemulsion was obtained containing 0.21% IPBC and 0.09% 8-Hydroxyquinoline. This microemulsion has remained clear after one month.

EXAMPLE 17

10 g of propyl-4-hydroxy benzoate, (CAS-94-13-3), and 10 g iodopropynyl butyl carbamate were dissolved by stirring and heating to 45° C. in 80 g Cremophor El.

A clear solution was obtained containing a total of 20% active ingredients. It remains clear on cooling and aging.

5 gm of this solution was added to 95 gm water and the mixture agitated to obtain a very slightly opalescent clear solution containing 0.5% propyl-4-hydroxy benzoate and 0.5% iodopropynyl butyl carbamate. This solution has remained stable for 4 weeks.

EXAMPLE 18

7.5 g o-phenylphenol, (CAS-90-43-7) and 7.5 g iodopropynyl butyl carbamate were added to 85 g Cremophor El.

The mixture was stirred and heated to 50° C. until a clear solution was obtained. This solution remains clear on cooling to room temperature and aging.

4 gm of this solution were added to 96 g water to yield a clear microemulsion.

EXAMPLE 19

10 g o-phenyl phenol was dissolved in 90 g Cremophor El by stirring and warming to 60° C. A clear solution containing 10% o-phenylphenol is obtained.

3 g of this solution was stirred into 97 g water to yield a clear microemulsion that remained stable for at least one month, and contains 0.3 % o-phenylphenol.

While certain specific embodiments of the invention have been described with particularity herein, it will be recognized that various modifications thereof will occur to those skilled in the art and it is to be understood that such modifications and variations are to be included within the preview of this application and the spirit and scope of the appended claims.

I claim:

1. A water miscible biocidal composition suitable for forming a microemulsion, a micellar solution or a molecular solution consisting of a solvating surfactant selected from the group consisting of an alkoxylated castor oil, an alkoxylated hydrogenated castor oil and an alkoxylated rosin, and a biocidal biologically active material dissolved in said solvating surfactant.

2. The composition of claim 1 wherein the solvating surfactant is selected from the group consisting of an ethoxylated castor oil, an ethoxylated hydrogenated castor oil and an ethoxylated rosin.

3. The composition of claim 1 wherein the biocidal biologically active material is selected from iodopropargyl butyl carbamate; benzisothiazolones; permethryn; terbutryn; propaconazole; tebuconazole; 8-hydroxyquinoline; propiconazole; deltamethrin; cypermethrin; chlorpyriphos; 2-(hydroxymethylamino) ethanol; iodopropynyl cyclohexyl carbamate; N-cyclopropynyl-$N^1$-(1,1-dimethylethyl)-6-(methylthio)-1,3,5-triazine-2,4-diamine; 2,4-dichloro phenoxyacetic acid, butyl ester; 2,4,5-trichlorophenoxy acetic acid, ethyl ester; 2,4 dichlorbutyric acid, ethyl ester; Chlordane; piperonyl butoxide; bromoxynil; isobornylthiocyanoacetate; iodo propargyl succinate; 5-chloro-2-methyl-4-isothiazolin-3-one; 2-methyl-4-isothiazolin-3-one; 1,4-dichloro-2,5-dimethoxy benzene; orthophenylphenol; azaconazole; cyperconazole; diiodomethyl-p-tolyl sulfone; iodopropynyl phenylether; Cyfluthrin; beta cyfluthrin; lambda-cyhalothrin; cyhexatin; cyphenothrin; endosulfan; (1,4,5,6,7,7-hexachloro 8,9,10-trinorborn-5-en-2,3-ylene bismethylene) sulfide and fenitrothion.

4. The composition of claim 3 also containing a co-solvent.

5. The composition of claim 4 wherein said co-solvent is castor oil.

6. The composition of claim 5 wherein the biocidal active material comprises 5 to 25 weight percent of said composition.

7. An aqueous biocidal composition of a microemulsion, a micellar solution or a molecular solution prepared by mixing water and a biocidal composition consisting essentially of a solvating surfactant selected from the group consisting of an alkoxylated castor oil, an alkoxylated hydrogenated castor oil and an alkoxylated rosin, and a biocidal biologically active material dissolved in said solvating surfactant.

8. The aqueous composition of claim 7 wherein the solvating surfactant is selected from the group consisting of an ethoxylated castor oil, an ethoxylated hydrogenated castor oil and an ethoxylated rosin.

9. The aqueous composition of claim 8 wherein the biocidal biologically active material is selected from the biocidal biologically active material is selected from iodopropargyl butyl carbamate; benzisothiazolones; permethryn; terbutryn; propaconazole; tebuconazole; propiconazole; deltamethrin; cypermethrin; chlorpyriphos; 8-hydroxyquinoline; 2-(hydroxymethylamino) ethanol; iodopropynyl cyclohexyl carbamate; N-cyclopropynyl-$N^1$-(1,1-dimethylethyl)-6 -(methylthio)-1,3,5-triazine-2,4-diamine; 2,4-dichloro phenoxyacetic acid, butyl ester; 2,4, 5-trichlorophenoxy acetic acid, ethyl ester; 2,4 dichlorbutyric acid, ethyl ester; Chlordane; piperonyl butoxide; bromoxynil; isobornylthiocyanoacetate; iodo propargyl succinate; 5-chloro-2-methyl-4-isothiazolin-3-one; 2-methyl-4-isothiazolin-3-one; 1,4-dichloro-2,5-dimethoxy benzene; orthophenylphenol; azaconazole; cyperconazole; diiodomethyl-p-tolyl sulfone; iodopropynyl phenylether; Cyfluthrin; beta cyfluthrin; lambda-cyhalothrin; cyhexatin; cyphenothrin; endosulfan; (1,4,5,6,7,7-hexachloro 8,9,10-trinorborn-5-en-2,3-ylene bismethylene) sulfide and fenitrothion.

10. The aqueous composition of claim 8 also containing a co-solvent.

11. The aqueous composition of claim 10 wherein said co-solvent is castor oil.

12. The aqueous composition of claim 10 wherein the biocidal active material comprises 5 to 25 weight percent of said composition.

13. A method for forming a microemulsion, a micellar solution or a molecular solution having a biocidal biological activity which comprises mixing with water a biocidal composition consisting essentially of a solvating surfactant selected from the group consisting of an alkoxylated castor oil, an alkoxylated hydrogenated castor oil and an alkoxylated rosin, and a biocidal biologically active material dissolved in said solvating surfactant.

14. The method of claim 13 wherein the solvating surfactant is selected from the group consisting of an ethoxylated castor oil, an ethoxylated hydrogenated castor oil and an ethoxylated rosin.

15. The method of claim 13 wherein the biocidal biologically active material is selected from iodopropargyl butyl carbamate; benzisothiazolones; permethryn; terbutryn; propaconazole; tebuconazole; propiconazole; deltamethrin; cypermethrin; chlorpyriphos; 8-hydroxyquinoline; 2-(hydroxymethylamino) ethanol; iodopropynyl cyclohexyl carbamate; N-cyclopropynyl-$N^1$-(1,1-dimethylethyl)-6-(methylthio)-1,3,5-triazine-2,4-diamine; 2,4-dichloro phenoxyacetic acid, butyl ester; 2,4,5-trichlorophenoxy acetic acid, ethyl ester; 2,4 dichlorbutyric acid, ethyl ester; Chlordane; piperonyl butoxide; bromoxynil; isobornylthiocyanoacetate; iodo propargyl succinate; 5-chloro-2-methyl-4-isothiazolin-3-one; 2-methyl-4-isothiazolin-3-one; 1,4-dichloro-2,5-dimethoxy benzene; orthophenylphenol; azaconazole; cyperconazole; diiodomethyl-p-tolyl sulfone; iodopropynyl phenylether; Cyfluthrin; beta cyfluthrin; lambda-cyhalothrin; cyhexatin; cyphenothrin; endosulfan; (1,4,5,6,7,7-hexachloro 8,9,10-trinorborn-5-en-2,3-ylene bismethylene) sulfide and fenitrothion.

16. The method of claim 15 wherein the biocidal active material comprises 5 to 25 weight percent of said microemulsion, micellar solution, or molecular solution.

* * * * *